United States Patent [19]

Yamamuro

[11] Patent Number: 4,954,534
[45] Date of Patent: Sep. 4, 1990

[54] PHOTODECOMPOSING ORGANOSILICON COMPOUNDS AND PHOTOPOLYMERIZABLE EPOXY RESIN COMPOSITIONS CONTAINING THE ORGANOSILICON COMPOUNDS

[75] Inventor: Tetsu Yamamuro, Yamato, Japan

[73] Assignee: Ricoh Company, Ltd., Tokyo, Japan

[21] Appl. No.: 219,193

[22] Filed: Jul. 15, 1988

[30] Foreign Application Priority Data

Jul. 23, 1987 [JP] Japan .................. 62-185061
Jul. 23, 1987 [JP] Japan .................. 62-185062

[51] Int. Cl.$^5$ .................. C08G 58/70; C07F 7/10
[52] U.S. Cl. .................. 522/28; 522/170; 556/416; 556/417; 556/422
[58] Field of Search .................. 522/28; 556/416, 417, 556/422

[56] References Cited

U.S. PATENT DOCUMENTS

| | | | |
|---|---|---|---|
| 4,476,290 | 10/1984 | Hayase et al. .................. | 522/65 |
| 4,495,042 | 1/1985 | Hayase et al. .................. | 522/28 |
| 4,599,155 | 7/1986 | Suzuki et al. .................. | 522/28 |
| 4,816,496 | 3/1989 | Wada et al. .................. | 522/17 |
| 4,831,063 | 5/1989 | Suzuki .................. | 522/13 |

*Primary Examiner*—John C. Bleutge
*Assistant Examiner*—Arthur H. Koeckert
*Attorney, Agent, or Firm*—Oblon, Spivak, McClelland, Maier & Neustadt

[57] ABSTRACT

An organosilicon compound having general formula (I)

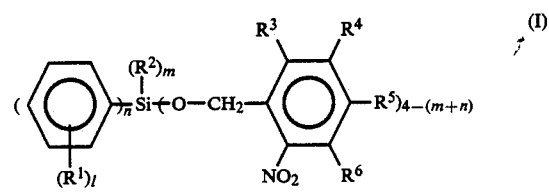

wherein $R^1$ represents fluorine; l is an integer of 1 to 5; $R^2$ represents a lower alkyl group, a lower unsaturated alkyl group or an aromatic group, $R^3$, $R^4$, $R^5$ and $R^6$ each represent hydrogen, halogen, an alkyl group, an aryl group, a nitro group, a cyano group, and an alkoxyl group, which may be the same or different; m is an integer of 0 to 2, when m is 2, each $R^2$ may be the same or different; and n is an integer of 1 to 3, provided that m+n is not more than 3 (m+n≦3), and a photopolymerizable epoxy resin composition prepared by mixing an epoxy resin component, the above photodecomposing organosilicon compound, and an aluminum compound are disclosed.

9 Claims, 1 Drawing Sheet

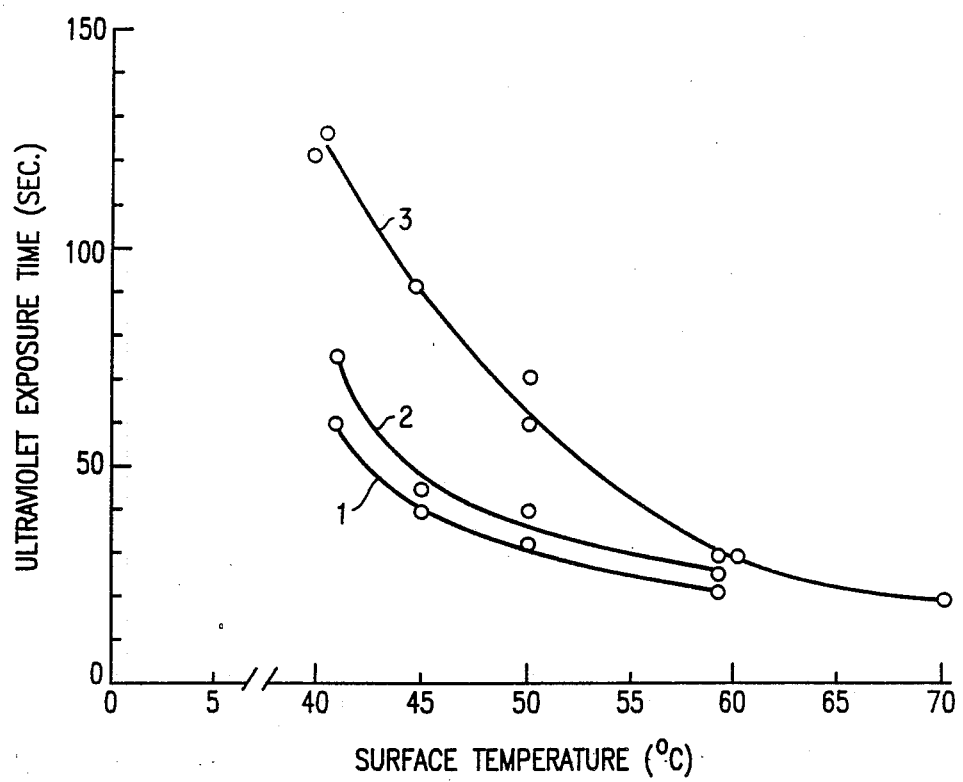

PHOTODECOMPOSING ORGANOSILICON COMPOUNDS AND PHOTOPOLYMERIZABLE EPOXY RESIN COMPOSITIONS CONTAINING THE ORGANOSILICON COMPOUNDS

BACKGROUND OF THE INVENTION

The present invention relates to photodecomposing organosilicon compounds and photopolymerizable epoxy resin compositions containing the organosilicon compounds.

Recently, photosetting processes for curing resins are attracting much attention from the viewpoint of energy saving and improvement on working efficiency. Among the photosetting processes, in particular, a curing process of photopolymerizing epoxy resin in the presence of a catalyst composed of a photodecomposing organosilicon compound and a metal complex has wide application and has the following advantages over other processes:

(a) Satisfactory photosetting can be performed by photopolymerization and the cured products obtained by this process have excellent electric characteristics as reported in "Nippon Kagaku Kaishi" 1985, (3), p.328–333.

(b) This process enables the production of reliable materials for use in optical information recording medium in a short curing time with high productivity.

(c) This process provides an adhesive agent suitable, for example, for devices using liquid crystals.

Varieties of photopolymerizable epoxy resin compositions have been proposed. For example, Japanese Laid-Open Patent Application No. 61-221 discloses a composition in which an organosilicon compound having the following general formula (I) and an aluminum compound are blended together with epoxy resin. The thus blended epoxy resin is evaluated as having particularly high photo-setting speed ("Nippon Kagaku Kaishi" 1985, (3), p.328–333).

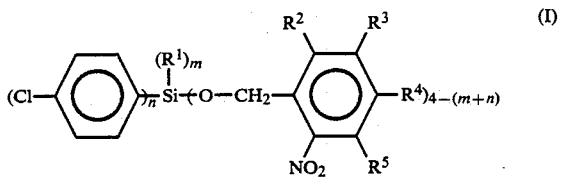

wherein $R^1$ represents a lower alkyl group, a lower unsaturated alkyl group or an aromatic group; $R^2$, $R^3$, $R^4$ and $R^5$ each represent hydrogen, halogen, or an organic group such as an alkyl group, an aryl group, a nitro group, a cyano group, and an alkoxyl group, which may be the same or different; m is an integer of 0 to 2; and n is an integer of 1 to 3, provided that m+n is not more than 3 ($m+n \leq 3$).

Japanese Laid-Open Patent Application No. 58-174389 describes in detail the photodecomposing organosilicon compounds having the above-mentioned structure and a method of producing the same.

The photopolymerizable epoxy resin compositions prepared by the above-mentioned conventional methods are excellent in electric characteristics and resistant to corrosion, but have the shortcomings that the photo-setting speed is low at low temperatures and accordingly the productivity thereof is too low for actual production.

In the case of the above conventional photopolymerizable epoxy resin compositions, their photo-setting speed can be increased by raising the photo-setting temperature. However, when the photo-setting temperature is raised too much, the temperature of other materials which are in contact with the epoxy resin compositions is also raised, with the result that physical changes may occur in some of the materials, which may also cause the production of improper products. In addition, these compositions have another significant shortcoming that the pot-life is so short that workability is unsatisfactory.

SUMMARY OF THE INVENTION

It is therefore an object of the present invention to provide an organosilicon compound capable of quickly photo-setting an epoxy resin at low temperatures Another object of the present invention is to provide a photopolymerizable epoxy resin composition having an increased photo-setting speed at low temperatures and an extended pot-life, from which the above-described conventional drawbacks have been eliminated.

The first object of the present invention can be achieved by an organosilicon compound having the following formula (II):

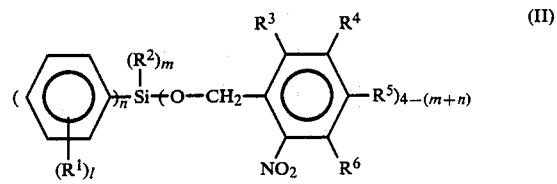

wherein $R^1$ represents fluorine; l is an integer of 1 to 5; $R^2$ represents a lower alkyl group, a lower unsaturated alkyl group or an aromatic group, $R^3$, $R^4$, $R^5$ and $R^6$ each represent hydrogen, halogen, an alkyl group, an aryl group, a nitro group, a cyano group, and an alkoxyl group, which may be the same or different; m is an integer of 0 to 2, when m is 2, each $R^2$ may be the same or different; and n is an integer of 1 to 3, provided that m+n is not more than 3 ($m+n \leq 3$).

The above organosilicon compound corresponds to such a compound that the chlorine in the previously mentioned conventional organosilicon compound of general formula (I) is replaced by fluorine.

The second object of the present invention can be achieved by a photopolymerizable epoxy resin composition which is prepared by adding to an epoxy resin the photo-decomposing organosilicon compound of the above formula (II) and an aluminum compound.

BRIEF DESCRIPTION OF THE DRAWING

In the drawing, the single figure is a graph showing the relationship between the ultraviolet exposure time required for photo-setting each of a photopolymerizable epoxy resin composition No. 1 according to the present invention and comparative photopolymerizable epoxy resin compositions No. 1 and No. 2 and the surface temperature thereof.

DETAILED DESCRIPTION OF THE PREFERRED EMBODIMENTS

As mentioned above, the organosilicon compound according to the present invention is represented by the following formula (II).

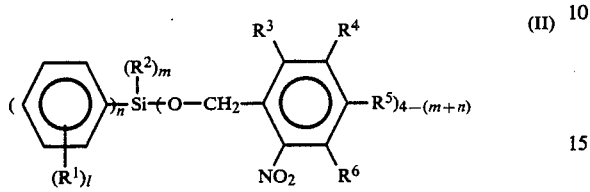
(II)

wherein $R^1$ represents fluorine; $l$ is an integer of 1 to 5; $R^2$ represents a lower alkyl group, a lower unsaturated alkyl group or an aromatic group, $R^3$, $R^4$, $R^5$ and $R^6$ each represent hydrogen, halogen, an alkyl group, an aryl group, a nitro group, a cyano group, and an alkoxyl group, which may be the same or different; m is an integer of 0 to 2, when m is 2, each $R^2$ may be the same or different; and n is an integer of 1 to 3, provided that m +n is not more than 3 (m+n≦3).

In the above formula (II), it is preferable that the lower alkyl group or lower unsaturated alkyl group represented by $R^2$ have 1 to 6 carbon atoms, which may have as a substituent a halogen atom, preferably fluorine. Further, it is preferable that the aromatic group represented by R2 be an aryl group such as a phenyl group and a tolyl group, which may have a substitutent such as halogen, an alkyl group, an aryl group, a nitro group, a cyano group and an alkoxyl group.

Repesentative examples of the organosilicon compound of general formula (II) according to the present invention are as follows:

dimethyl(p-fluorophenyl)(o-nitrobenzyloxy)silane (1)

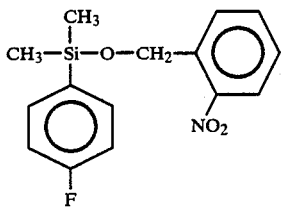

bis(p-fluorophenyl)methyl(o-nitrobenzyloxy)silane (2)

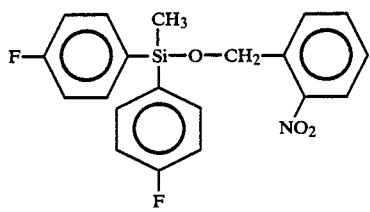

tris(p-fluorophenyl)(o-nitrobenzyloxy)silane (3)

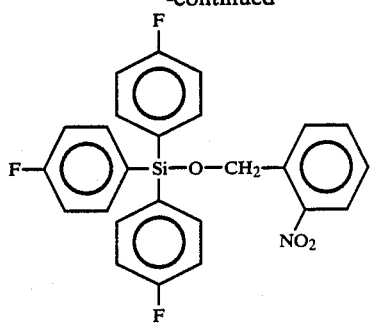

tris(2,4,6-trifluorophenyl)(o-nitrobenzyloxy)silane (4)

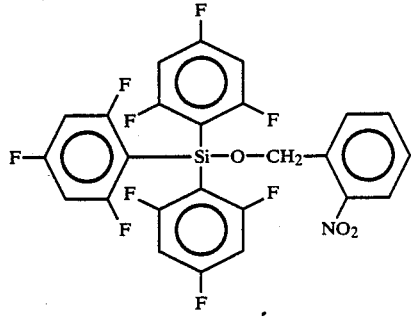

tris(2,4,5-trifluorophenyl)(o-nitrobenzyloxy)silane (5)

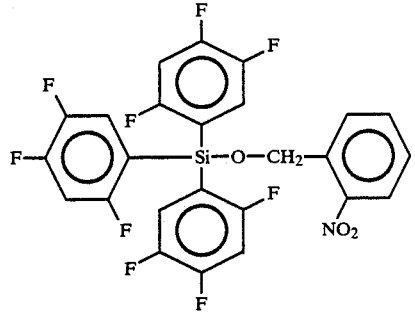

bis(p-fluorophenyl)(2-fluoroethyl)(o-nitrobenzyloxy)silane (6)

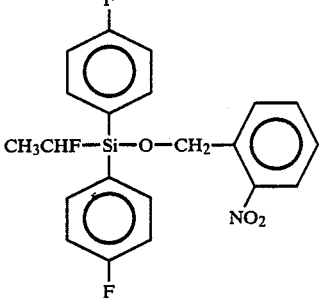

bis(p-fluorophenyl)bis(o-nitrobenzyloxy)silane (7)

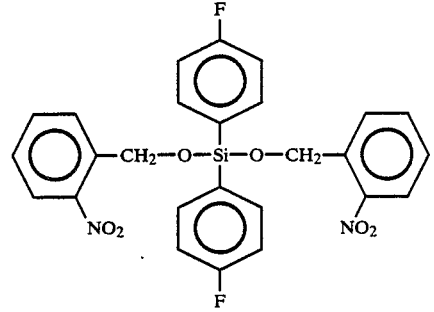

-continued (p-fluorophenyl)methylbis(o-nitrobenzyloxy)silane (8)

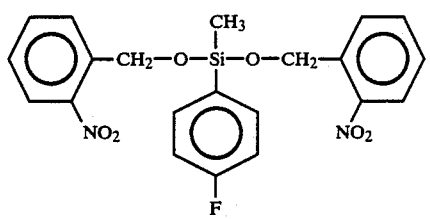

(p-fluorophenyl)tri(o-nitrobenzyloxy)silane (9)

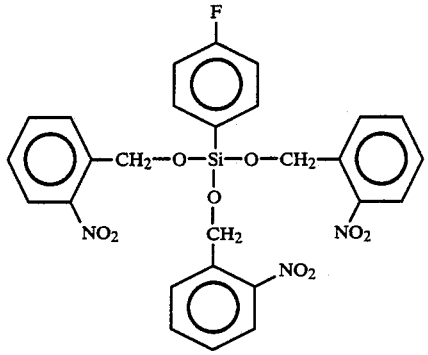

tris(p-fluorophenyl)(2,6-dinitrobenzyloxy)silane (10)

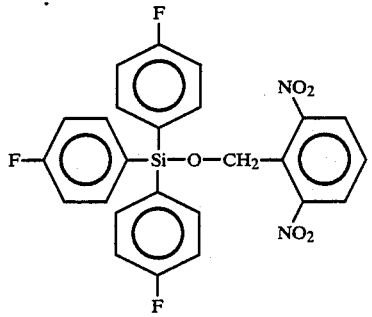

(2,4,6-trifluorophenyl)dimethyl(4,5-dimethoxy-2-nitrobenzyloxy)silane (11)

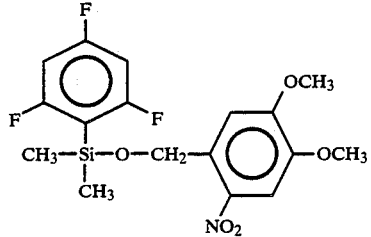

bis(p-fluorophenyl)methyl(4,5,6-trimethoxy-2-nitrobenzyloxy)silane (12)

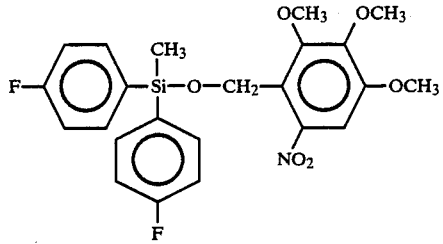

bis(p-fluorophenyl)methyl(3,4,5-trimethoxy-2-nitrobenzyloxy)silane (13)

-continued

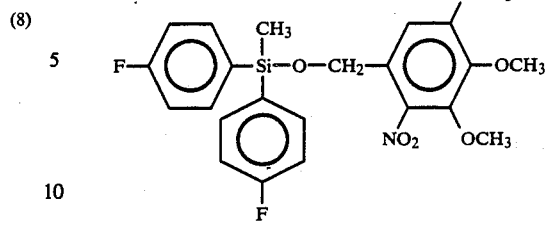

(2,4,5-trifluorophenyl)methylbis(p-chloro-o-nitrobenzyloxy)silane (14)

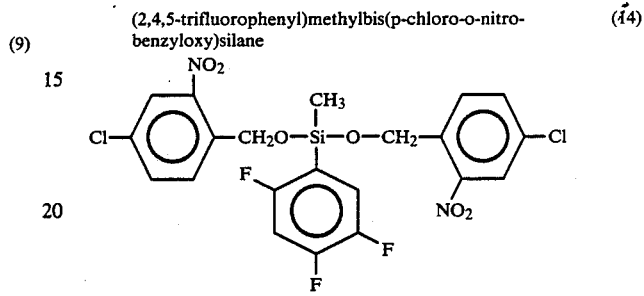

tris(p-flourophenyl)(p-phenoxy-o-nitrobenzyloxy)silane (15)

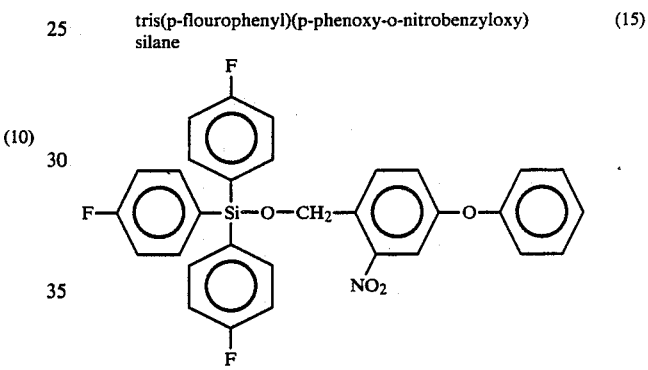

bis(p-fluorophenyl)vinyl(o-nitrobenzyloxy)silane (16)

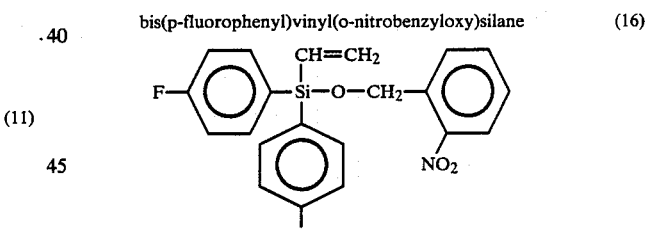

(p-fluorophenyl)methylvinyl(o-nitrobenzyloxy)silane (17)

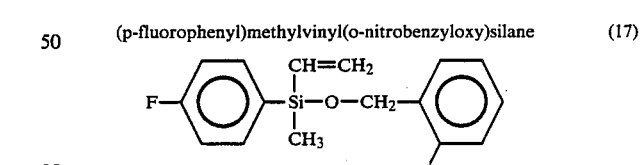

(p-fluorophenyl)vinylbis(o-nitrobenzyloxy)silane (18)

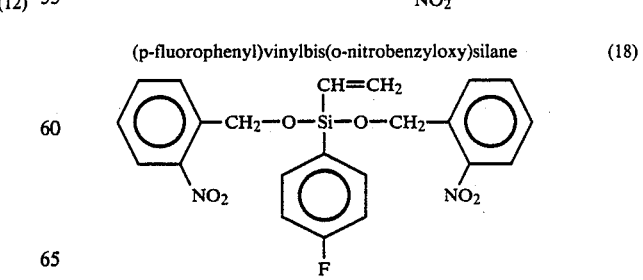

(2,4,6-trifluoropheny)-t-butylbis(o-nitrobenzyloxy)silane (19)

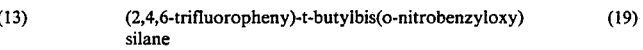

-continued

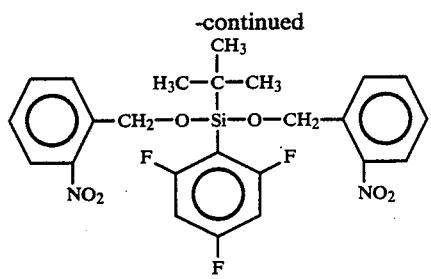

bis(p-fluorophenyl)bis(3-methyl-2-nitrobenzyloxy)silane (20)

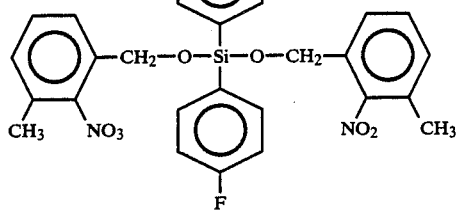

tris(p-fluorophenyl)(5-methyl-2-nitrobenzyloxy)silane (21)

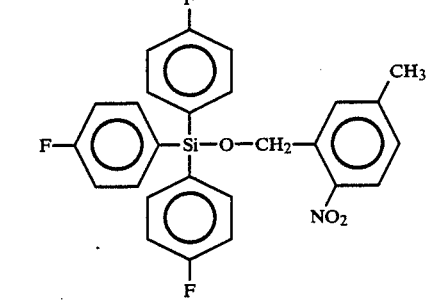

bis(2,4,5-trifluorophenyl)bis(3-methoxy-2-nitrobenzyloxy)silane (22)

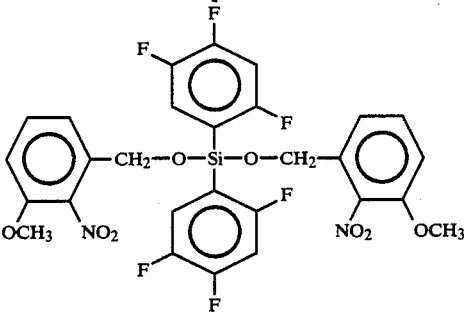

bis(p-flourophenyl)bis(6-chloro-2-nitrobenzyloxy)silane (23)

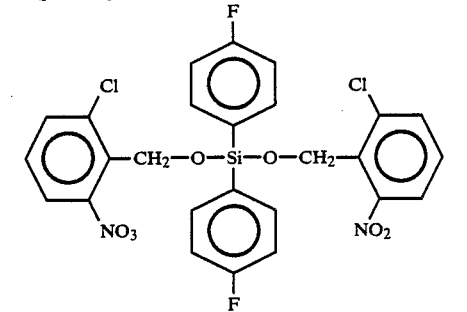

bis(p-fluorophenyl)bis(2,4-dinitrobenzyloxy)silane (24)

-continued

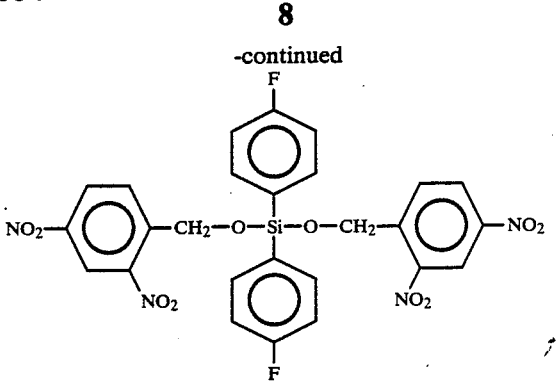

bis(p-fluorophenyl)phenyl(3-methyl-4-methoxy-2-nitrobenzyloxy)silane (25)

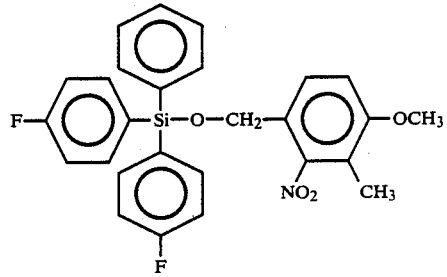

tris(p-fluorophenyl)(3,4-dimethoxy-2-nitro-benzyloxy)silane (26)

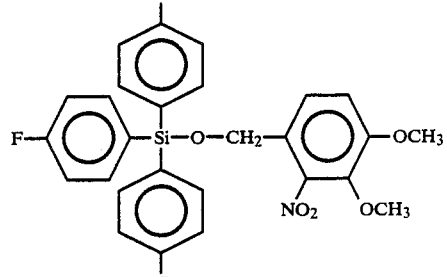

bis(p-fluorophenyl)phenyl(o-nitrobenzyloxy)silane (27)

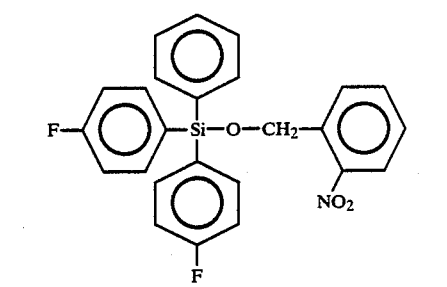

(p-fluorophenyl)diphenyl(o-nitrobenzyloxy)silane (28)

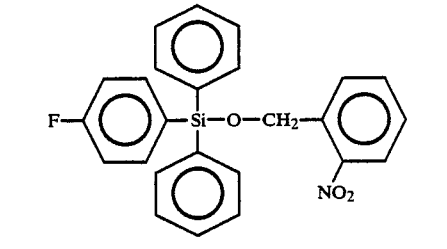

bis(2,4,6-trifluorophenyl)phenyl(o-nitrobenzyloxy)silane (29)

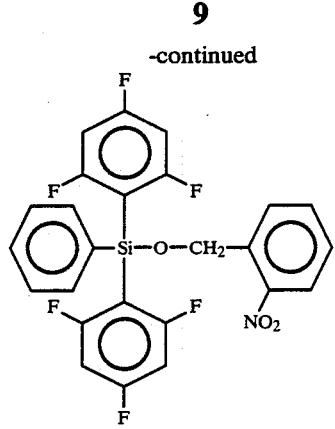

(2,4,6-trifluorophenyl)diphenyl(o-nitro-benzyloxy)silane (30)

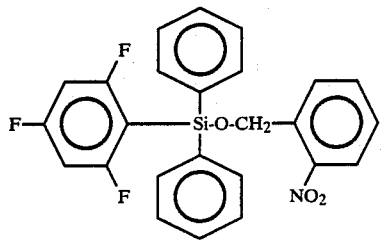

bis(2,4,5-trifluorophenyl)phenyl(o-nitro-benzyloxy)silane (31)

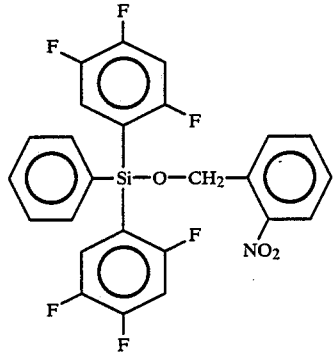

(2,4,5-trifluorophenyl)diphenyl(o-nitro-benzyloxy)silane (32)

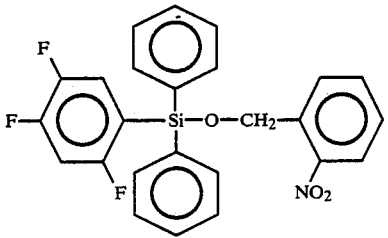

In addition to the above compounds, the following organosilicon compounds are also representative examples of the organosilicon compound of the general formula (II) according to the present invention:

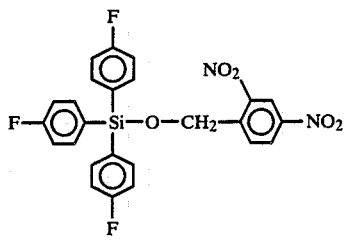
(33)

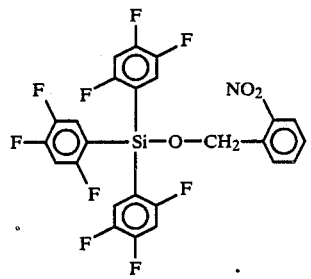
(34)

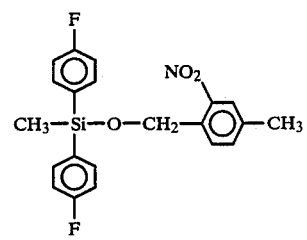
(35)

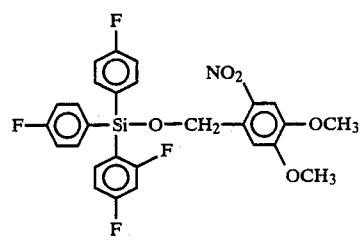
(36)

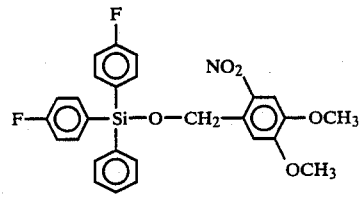
(37)

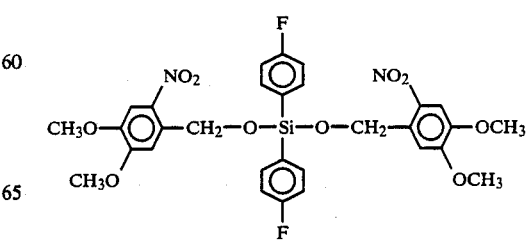
(38)

-continued

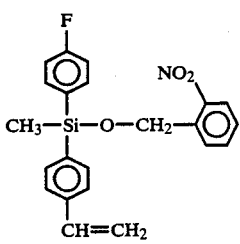

(39)

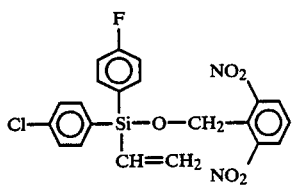

(40)

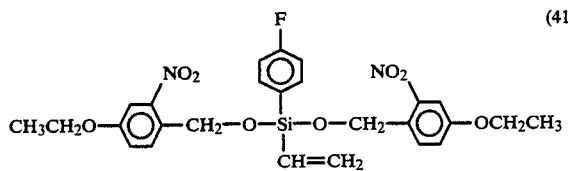

(41)

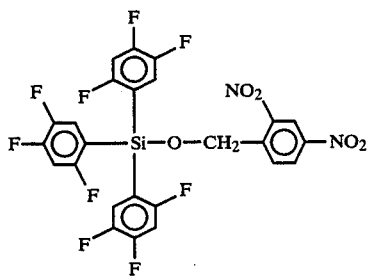

(42)

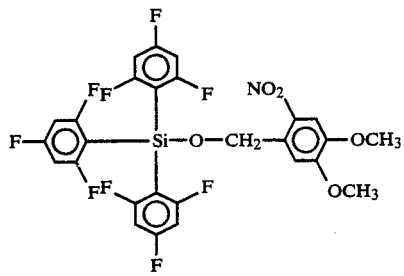

(43)

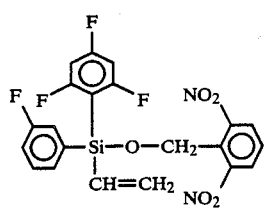

(44)

The photodecomposing organosilicon compounds according to the present invention can be prepared by the following method as described in Japanese Laid-Open Patent Application No. 58-174389:

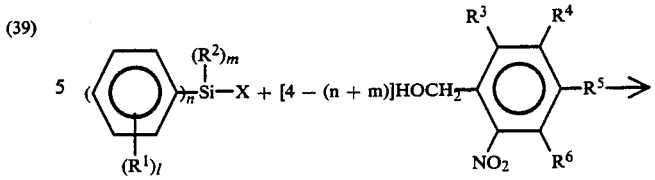

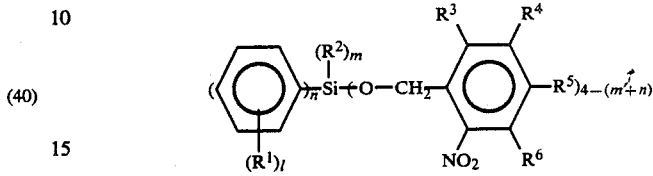

wherein X represents halogen, and $R^1$ through $R^6$, m, n, and are respectively the same as those defined in the previously mentioned general formula (II).

The above reaction can be carried out by allowing the above mentioned components to react in tetrahydrofuran in the presence of a base such as triethylamine at 60° C. to 70° C. for 0.5 to 48 hours.

The photodecomposing organosilicon compound according to the present invention is capable of serving as a catalyst for the photo-setting of an epoxy resin in combination with an aluminum compound.

A photopolymerizable epoxy resin composition according to the present invention comprises the above photo-decomposing organosilicon compound and the aluminum compound.

As the aluminum compound for use in the present invention, various organic complex compounds of aluminum are employed, and as the epoxy resin for use in the present invention, varieties of epoxy compounds having two or more epoxy groups in each monomer unit thereof are employed.

It is preferable that the amount of the photodecomposing organosilicon compound in the photopolymerizable epoxy resin composition according to the present invention be in the range of 0.5 to 15 parts by weight, and more preferably in the range of 1 to 12 parts by weight, to 100 parts by weight of the epoxy resin component.

When the photopolymerizable epoxy resin composition according to the present invention is prepared, an orthonitrobenzyl silyl ether compound having the following general formula (III) may be additionally used in combination with the photodecomposing organosilicon compound of the general formula (II) according to the present invention in order to increase the photo-setting speed of the photopolymerizable epoxy resin composition, without decreasing the pot-life of the photopolymerizable epoxy resin composition:

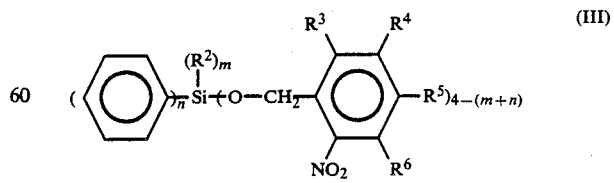

(III)

wherein $R^2$ through $R^6$, m, and n are respectively the same as those defined in the general formula (II).

Specific examples of the ortho-nitrobenzyl silyl ether compound of the general formula (III) are (o-nitrobenzyloxy)triphenylsilane and bis(o-nitrobenzyloxy) diphenylsilane.

When the o-nitrobenzyl silyl ether compound of the general formula (III) is employed in combination with the photodecomposing organosilicon compound of the general formula (II), it is preferable that the amount of the o-nitrobenzyl silyl ether compound be 0.1 to 1.5 times, and more preferably 0.2 to 1.0 times, the amount of the photodecomposing organosilicon compound of the general formula (II).

Therefore, when the o-nitrobenzyl silyl ether compound is used in combination with the photodecomposing organosilicon compound, it is preferable that the total amount of such organosilicon compounds be in the range of 0.55 to 37.5 parts by weight, more preferably in the range of 0.60 to 30 parts by weight, to 100 parts by weight of the epoxy resin component. In the above-mentioned ranges, the more the total amount of the organosilicon compounds represented by the formula (II) and the formula (III), the greater the photo-setting speed.

As mentioned previously, the epoxy resin for use in the photopolymerizable epoxy resin composition according to the present invention has two or more epoxy groups in each monomer unit thereof. Specific examples of the epoxy resin are roughly classified into the following 7 groups:

type Hydantoin-type and TGIC-type are included in this type.

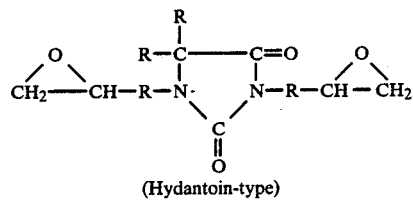

(Hydantoin-type)

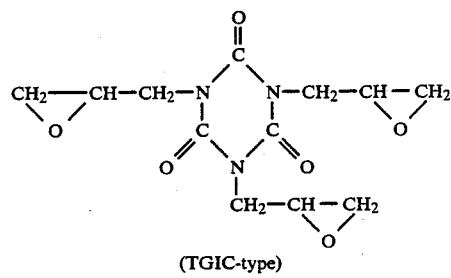

(TGIC-type)

Representative examples of commercially available epoxy resins of the above-mentioned types that can be employed in the present invention are as follows:

Araldite AY101, AZ102, AY103, AY105, AW106, (a) Bisphenol A - epichlorohydrin type

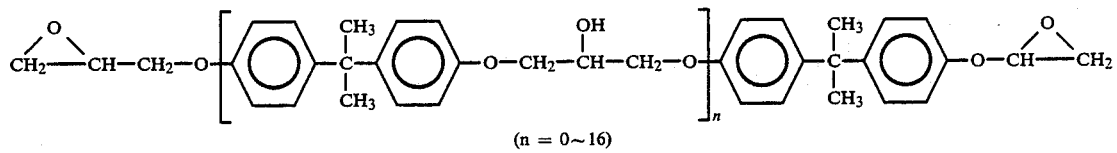

(n = 0~16)

(b) Novolak type

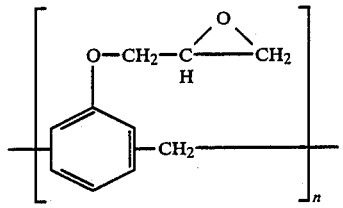

Epoxy resin having cycloaliphatic structure (Compounds having a cycloaliphatic epoxy group represented by

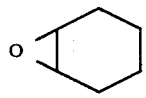

in one mononer unit thereof)

(d) Long-chain aliphatic series type

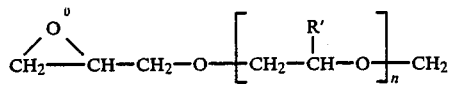

(e) Brominated epoxy resin A resin made of brominated bisphenol A. (f) Glycidyl ester type (g) Heterocyclic AV121N, AV121B, AV123B, AV129, AW134, AW136H, AW136N, AW1201, AV138, AY101, AY103, AT1 and AZ15; GY250, 260, 6071 and 6099; ECN1280; and CY208, 8011, 192, 2350 and 362 made by Ciba-Geigy, Ltd.; Lixon Bond 1001A, 1002A and 1004A made by Chisso Corporation; Dinacol EX-810, 811 851, 830, 832, 841, 861, 911, 941, 920, 921, 931, 211, 212 221 and 721; Dinacol EX-313, 314, 321, 411, 421, 521, 611, 612, 614, 614B and 622 made by Nagase & Co., Ltd.; Epicote 152, 828 and 1001 made by Yuka Shell Epoxy, K.K.; ERL4221 made by Union Carbide Japan K.K.; and EHPE-3150 made by Daicel Chemical Industries, Ltd.

The above-mentioned epoxy resins can be used alone or in combination.

Specific examples of commercially available epoxy resins having the cycloaliphatic structure are as follow:

Celloxide 2021, 2000, 3000, EHPE-3150-1 and Spiro-epoxy made by Daicel Chemical Industries, Ltd.; ERL4206, 4289, 4299 and 4234 made by Union Carbide Japan K.K.; Araldite CY177 and 179 made by Ciba-Geigy, Ltd.; vinylcyclohexane epoxide; and vinylcyclohexane diepoxide.

Representative examples of the above epoxy compound having the cycloaliphatic structure are as follows:

The above-mentioned epoxy compounds having the cycloaliphatic structure can be used alone or in combination. Alternatively, such epoxy compounds can be used in combination with the epoxy compounds not having the cycloaliphatic structure such as "EHPE-3150", made by Daicel Chemical Industries, Ltd., hav-

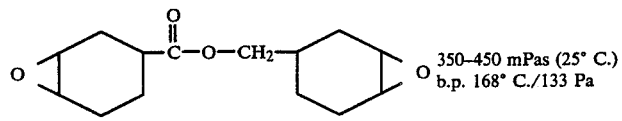

"Celloxide 2021"

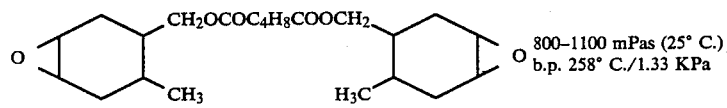

"ERL 4289"

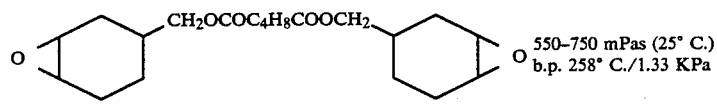

"ERL 4299"

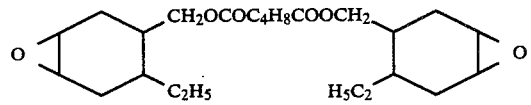

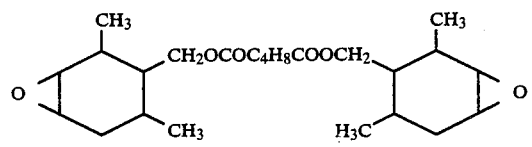

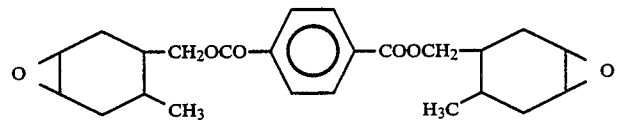

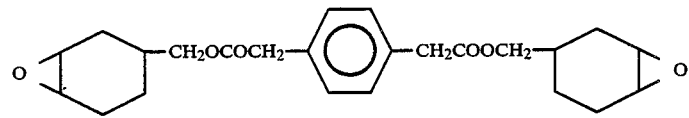

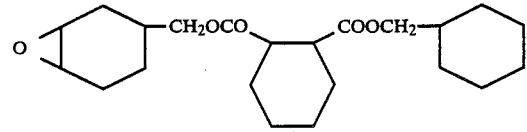

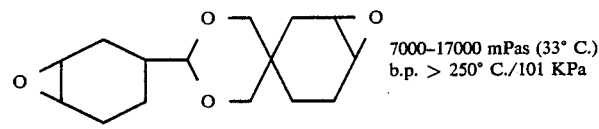

"ERL 4234" (made by Union Carbide Japan K.K., the same as "CY175" made by Ciba-Geigy, Ltd.)

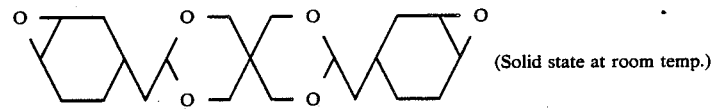

"Spiroepoxy" (made by Daicel Chemical Industries, Ltd.)

(Solid state at room temp.)

ing the following formula, and the bisphenol A - epichlorohydrin type epoxy resin such as "Epicote 828" made by Yuka Shell Epoxy, K.K.

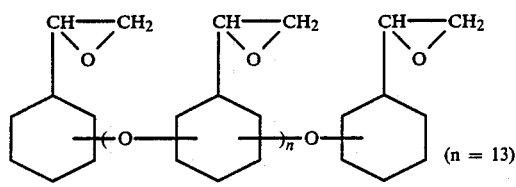 (n = 13)

Specific examples of the aluminum compound for use in the photopolymerizable epoxy resin composition according to the present invention are, for example, tris(ethoxyacetylacetato)aluminum, tris(oxynato)aluminum, trismethoxy aluminum, trisethoxy aluminum, trisisopropoxy aluminum, trisphenoxy aluminum, isopropoxy diethoxy aluminum, trisbutoxy aluminum, trisacetoxy aluminum, trisstearato aluminum, trisbutylato aluminum, trispropionato aluminum, trisisopropionato aluminum, trisacetylacetonato aluminum, tristrifluoroacetylacetonato aluminum, trispentafluoroacetylacetonato aluminum, trisethylacetoacetato aluminum, trissalicylaldehydato aluminum, trisdiethylmalorato aluminum, trispropylacetoacetato aluminum, trisbutylacetoacetato aluminum, trisdipivaloylmethanato aluminum, diacetylacetonato dipivaloylmethanato aluminum, tris(ethylacetoacetonato)aluminum, tris(tert-butylacetoacetato)aluminum, tris(isobutylacetoacetato)aluminum, tris(ethylsalicylato)aluminum, tris(phenylsalicylato)aluminum and tris(o-acetylphenolato)aluminum.

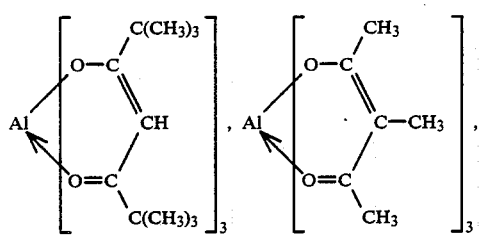

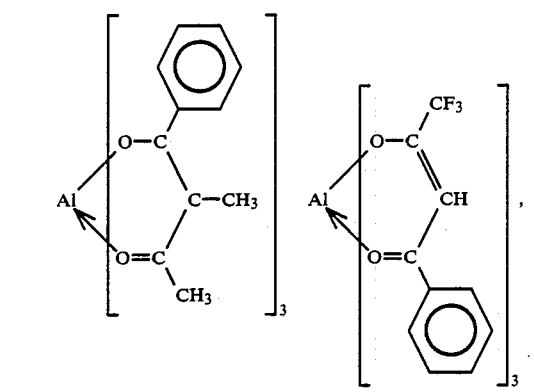

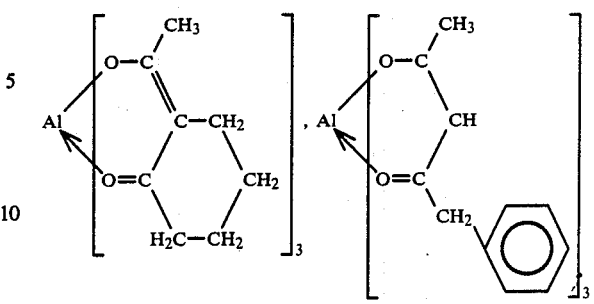

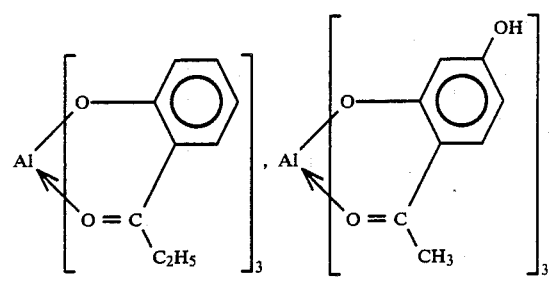

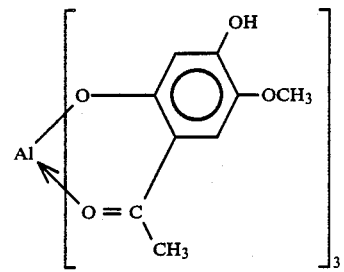

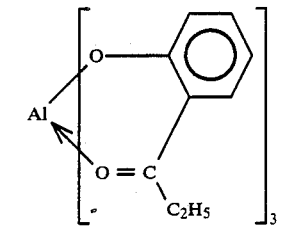

The above-mentioned aluminum compounds can be used alone or in combination. It is preferable that the amount of the aluminum compound be in the range of 0.01 to 10 parts by weight, more preferably in the range of 0.5 to 5 parts by weight, to 100 parts by weight of the epoxy resin component.

The photodecomposing organosilicon compound according to the present invention is stable in the dark. However, when exposed to ultraviolet light, it is easily decomposed to form silanol. The thus formed silanol, in collaboration with the aluminum compound, initiates the polymerization of the epoxy compound. The photodecomposing organosilicon compound according to the present invention is capable of photo-setting the epoxy resin at a greater speed, as compared with the silicon compounds for use in conventional techniques. It is considered that this is because the electronegativity of the fluorine atom in the organosilicon compound according to the present invention is so greater that a silanol having higher acidity is synthesized than in the case of the chlorine-containing conventional silicon compounds.

The photopolymerizable epoxy resin composition according to the present invention is prepared, for example, by photo-setting the epoxy resin at room temperature, photo-setting the same under application of heat, or with postcuring after the photo-setting, and then put to practical use.

Normally the wavelength of the light for the photo-setting of epoxy resins is in the range of 200 to 500 nm, and a preferable wavelength of the light is in the range of 300 to 400 nm. The exposure time of the epoxy resin to the light, which may varies, depending on the composition of the epoxy resin and a type of the employed catalyst, is normally in the range of 5 seconds to 150 minutes, preferably in the range of 15 seconds to 6 minutes. When the above epoxy resin composition is prepared by photo-setting under application of heat, the temperature, which also varies, depending on the composition of the epoxy resin and a type of the employed catalyst, is normally in the range of 20° to 200° C., preferably in the range of 25° to 80° C.

As the light source, a high-pressure mercury vapor lamp, a carbon-arc lamp, a xenon lamp and an argon glow discharge tube can be used. When the epoxy resin composition is prepared by subjecting it to postcure after photo-setting, normally the postcure is performed at 20° to 180° C. within 10 hours, preferably at 25° to 120° C. within 5 hours, which also varies depending on the composition of the epoxy resin and a type of the employed catalyst.

The present invention will now be explained in more detail with reference to the following examples. These examples are given for illustration and are not intended to be limiting thereof.

Example 1-1 [Preparation of tris(p-fluorophenyl) (o-nitrobenzyloxy)silane (Compound No. 3)]

The following components were stirred in 40 ml of tetrahydrofuran (THF) at 69° C. for 7 hours.

| Tris(p-fluorophenyl)chlorosilane | 4.17 g (0.01196 mol) |
|---|---|
| o-nitrobenzyl alcohol | 1.833 g (0.01197 mol) |
| Triethylamine | 1.222 g (0.01207 mol) |

After the stirring, a salt separated out. The salt was removed from the above reaction mixture by filtration, and from the resulting solution, tetrahydrofuran was evaporated by an evaporator under application of pressure by a water jet pump. The resulting mixture was subjected to column chromatography, using a gel (Trademark "Wakogel C-300" made by Wako Pure Chemical Industries, Ltd.), and toluene as the developing solvent for separation of the product. Then the separated product was recrystallized from a mixed solvent of 80 ml of chloroform and 5 ml of hexane, and dried in vacuum for 8 hours. Thus, the desired compound was obtained in a 74% yield.

The obtained compound was subjected to NMR spectrum inspection of $^1$H-NMR in dichloroform (CDCl$_3$) at room temperature. The result was that signals were observed corresponding to the following $\delta$ (ppm): 5.23, 6.91 to 8.10. Furthermore, an IR spectrum of the compound was taken, which indicated absorption peaks at 3050, 2920, 1918, 1660, 1618, 1590, 1520, 1502, 1450, 1396, 1380, 1344, 1314, 1272, 1230, 1200, 1170, 1150, 1116, 1076, 1120, 954, 874, 836, 800, 730, 680, 650, 524 and 456 cm$^{-1}$.

The above-mentioned compound was identified as tris(p-fluorophenyl)(o-nitrobenzyloxy)silane by both of the $^1$H-NMR and the IR spectrum.

Example 2-1

Using the photodecomposing organosilicon compound, tris(p-fluorophenyl)(o-nitrobenzyloxy)silane, prepared in Example 1-1, a photopolymerizable epoxy resin composition No. 1 according to the present invention was prepared by mixing the following components.

|  | Parts by Weight |
|---|---|
| Epoxy resin (Trademark "ERL 4299" made by Union Carbide Japan K.K.) | 100 |
| Tris(ethylacetoacetato)aluminum | 1.5 |
| Tris(p-fluorophenyl)(o-nitrobenzyloxy) silane (Compound No. 3) | 6.8 |

In the above-mentioned composition, the photodecomposing organosilicon compound (compound No. 3) and the epoxy resin are equal in the number of moles.

Comparative Example 2-1

Example 2-1 was repeated except that 6.8 parts by weight of tris(p-fluorophenyl)(o-nitrobenzyloxy)silane in the photo-polymerizable epoxy resin composition No. 1 of Example 2-1 was replaced by 7.4 parts by weight of tris(p-chlorophenyl) (o-nitrobenzyloxy)silane, whereby a comparative photo-polymerizable epoxy resin composition No. 1 was prepared.

Comparative Example 2-2

Example 2-1 was repeated except that 6.8 parts by weight of tris(p-fluorophenyl)(o-nitrobenzyloxy)silane in the photo-polymerizable epoxy resin composition No. 1 of Example 2-1 was replaced by 6.0 parts by weight of triphenyl(o-nitrobenzyloxy)silane, whereby a comparative photopolymerizable epoxy resin composition No. 2 was prepared.

In the above photopolymerizable epoxy resin compositions, the photodecomposing organosilicon compounds and the epoxy resin compositions are also equal in the number of moles.

The thus obtained photopolymerizable epoxy resin composition No. 1 according to the present invention and comparative photopolymerizable epoxy resin compositions No. 1 and No. 2 were subjected to the following photo-setting test:

Each photopolymerizable epoxy resin composition was applied dropwise on the surface of a solid plate with a predetermined temperature and exposed to ultraviolet light. The ultraviolet light was separately taken out of the light from a high-pressure mercury lamp (Trademark "UVL-2000-OS" made by Ushio Inc.) by using a cold mirror which allows infrared light to pass therethrough and reflects ultraviolet light.

The relationship between the exposure time by ultraviolet light for the photo-setting of each composition at a position 16 cm away from the mercury lamp serving as the light source, and the surface temperature was shown in the accompanying Single Figure. In the Single Figure, curves 1, 2 and 3 respectively indicate the measurement results of the photopolymerizable epoxy resin composition No. 1 according to the present invention, and the comparative photopolymerizable epoxy resin compositions No. 1 and No. 2.

It is evident from the results of the photo-setting test, as shown in the Single Figure, that the photo-polymerizable epoxy resin composition No. 1 according to the present invention is improved in the photo-setting speed in the photo-setting reaction of epoxy resin, as compared with other conventional comparative compositions.

Example 1-2 [Preparation of tris(2,4,6-trifluorophenyl)(o-nitrobenzyloxy)silane (Compound No. 4)]

The following components were stirred in 40 ml of tetrahydrofulan (THF) at 65° C. for 17 hours.

| | |
|---|---|
| Tris(2,4,6-trifluorophenyl) chlorosilane | 3.00 g (0.006569 mol) |
| o-nitrobenzyl alcohol | 1.01 g (0.006597 mol) |
| Triethylamine | 0.72 g (0.00711 mol) |

After the stirring, a salt separated out. The salt was removed from the above reaction mixture by filtration, and from the resulting solution, tetrahydrofuran was evaporated by an evaporator under application of pressure by a water jet pump. The resulting mixture was subjected to column chromatography, using a gel (Trademark "Wakogel C-300" made by Wako Pure Chemical Industries, Ltd.), and toluene as the developing solvent for separation of the product. Then the separated product was recrystallized from 20 ml-hexane solution, and dried in vacuum for 9 hours. Thus, the desired compound was obtained in a 16.5% yield.

The obtained compound was subjected to NMR spectrum inspection of $^1$H-NMR in dichloroform (CDCl$_3$) at room temperature. The result was that signals were observed corresponding to the following δ(ppm): 5.30, 6.40, 6.54, 6.66; 7.11 to 8.10. Furthermore, an IR spectrum of the compound was taken, which indicated absorption peaks at 3125, 1640, 1616, 1549, 1532, 1428, 1382, 1350, 1296, 1202, 1174, 1154, 1110, 1080, 1024, 1006, 850, 800, 736, 660, 628, 520, 462 and 443 cm.$^{-1}$.

The above-mentioned compound was identified as tris(2,4,6-trifluorophenyl)(o-nitrobenzyloxy)silane by both of the $^1$H-NMR and the IR spectrum.

Example 2-2

Using the photodecomposing organosilicon compound, tris(2,4,6-trifluorophenyl)(o-nitrobenzyloxy)silane, prepared in Example 1-2, a photopolymerizable epoxy resin composition No. 2 according to the present invention was prepared by mixing the following components.

| | Parts by Weight |
|---|---|
| Epoxy resin (Trademark "ERL-4299" made by Union Carbide Japan K.K.) | 100 |
| Tris(ethylacetoacetato)aluminum | 1.55 |
| Tris(2,4,6-fluorophenyl)(o-nitrobenzyloxy)silane (Compound No. 4) | 8 |

The thus obtained photopolymerizable epoxy resin composition No. 2 was applied dropwise on a polycarbonate plate and exposed to ultraviolet light, at a position 12 cm away from the same high-pressure mercury lamp light source as that employed in Example 1-1. The result was that the photo-polymerizable epoxy resin composition No. 2 according to the present invention was completely photo-set in 45 seconds.

Example 2-3

Using the photodecomposing organosilicon compound, tris(4-fluorophenyl)(o-nitrobenzyloxy)silane, a photo-polymerizable epoxy resin composition No. 3 according to the present invention was prepared by mixing the following components.

| | Parts by Weight |
|---|---|
| Epoxy resin (Trademark "ERL 4299" made by Union Carbide Japan K.K.) | 8 |
| Tris(ethylacetoacetato)aluminum | 0.12 |
| Tris(4-fluorophenyl)(o-nitrobenzyloxy)silane | 0.55 |

The thus obtained photopolymerizable epoxy resin composition No. 3 was applied dropwise on a polycarbonate plate and exposed to ultraviolet light at a temperature of 40° C., at a position 16 cm away from the same high-pressure mercury lamp light source as that employed in Example 1-1. The result was that this photopolymerizable epoxy resin composition No. 3 according to the present invention was completely photo-set in 60 seconds. The above composition was allowed to stand at room temperature for 10 days to measure the pot-life thereof, with the result that no substantial changes occurred during that period of time.

Comparative Example 2-3

Example 2-3 was repeated except that tris(4-fluorophenyl)(o-nitrobenzyloxy)silane in the photo-polymerizable epoxy resin composition No. 3 of Example 2-3 was replaced by tris(4-chlorophenyl)(o-nitrobenzyloxy)silane, whereby a comparative photopolymerizable epoxy resin composition No. 3 was prepared.

The thus obtained comparative photopolymerizable epoxy resin composition No. 3 was subjected to the photo-setting test. The result was that the photopolymerizable epoxy resin composition No. 3 was completely photo-set in 75 seconds. The above composition was allowed to stand at room temperature for 7 days to measure the pot-life thereof, with the result that some changes were observed before 7 days.

Example 2-4

Using the photodecomposing organosilicon compound, tris(4-fluorophenyl)(o-nitrobenzyloxy)silane, a photo-polymerizable epoxy resin composition No. 4 according to the present invention was prepared by mixing the following components.

| | Parts by Weight |
|---|---|
| Epoxy resin A (Trademark "ERL 4299" made by Union Carbide K.K.) | 3.6 |
| Epoxy resin B (Trademark "EHPE-3150" made by Daicel Chemical Industries, Ltd.) | 1.2 |
| Epoxy resin C | 1.2 |

|  | Parts by Weight |
|---|---|
| (Trademark "Spiroepoxy" made by Daicel Chemical Industries, Ltd.) | |
| Tris(ethylacetoacetato)aluminum | 0.1 |
| Tris(4-fluorophenyl)(o-nitrobenzyloxy)silane | 0.5 |

The thus obtained photopolymerizable epoxy resin composition No. 4 was subjected to the photo-setting test and the pot-life test in the same manner as employed in Example 2-3 at a temperature of 45° C. The result was that the photo-polymerizable epoxy resin composition No. 4 according to the present invention was completely photo-set in 75 seconds. The pot-life thereof was 42 days and the viscosity of the resin increased with time thereafter.

Comparative Example 2-4

Example 2-4 was repeated except that 0.5 parts by weight of tris(4-fluorophenyl)(o-nitrobenzyloxy)silane in the photo-polymerizable epoxy resin composition No. 4 of Example 2-4 was replaced by 0.55 parts by weight of tris(4-chlorophenyl) (o-nitrobenzyloxy)silane, whereby a comparative photopolymerizable epoxy resin composition No. 4 was prepared.

The thus obtained comparative photopolymerizable epoxy resin composition No. 4 was subjected to the photo-setting test. The result was that the comparative photopolymerizable epoxy resin composition No. 4 was completely photo-set in 90 seconds.

The above composition was allowed to stand at room temperature to measure the pot-life thereof, with the result that the pot-life of this composition was 19 days.

Example 2-5

Using the photodecomposing organosilicon compound, tris(2,4,6-trifluorophenyl)(o-nitrobenzyloxy)silane, a photopolymerizable epoxy resin composition No. 5 according to the present invention was prepared by mixing the following components.

|  | Parts by Weight |
|---|---|
| Epoxy resin D (Trademark "Celloxide 2021" made by Daicel Chemical Industries, Ltd.) | 3.6 |
| Epoxy resin A (Trademark "EHPE-3150" made by Daicel Chemical Industries, Ltd.) | 1.2 |
| Epoxy resin C (Trademark "Spiroepoxy" made by Daicel Chemical Industries, Ltd.) | 1.2 |
| Tris(salicylaldehydato)aluminum | 0.11 |
| Tris(2,4,6-trifluorophenyl)(o-nitrobenzyloxy)silane | 0.55 |

The thus obtained photopolymerizable epoxy resin composition No. 5 was subjected to the photo-settting test and the pot-life test in the same manner as in Example 2-3 at a temperature of 45° C. The result was that the photo-polymerizable epoxy resin composition No. 5 according to the present invention was completely photo-set in 85 seconds The pot-life thereof was 20 days and the viscosity of the resin increased with time thereafter.

Comparative Example 2-5

Example 2-5 was repeated except that 0.55 parts by weight of tris(2,4,6-trifluorophenyl)(o-nitrobenzyloxy)silane in the photopolymerizable epoxy resin composition No. 5 of Example 2-5 was replaced by 0.60 parts by weight of tris(4-chlorophenyl)(o-nitrobenzyloxy)silane, whereby a comparative photopolymerizable epoxy resin composition No. 5 was prepared.

The thus obtained comparative photopolymerizable epoxy resin composition No. 5 was subjected to the photo-setting test and the pot-life test in the same manner as in Example 2-3 at a temperature of 45° C. The result was that the comparative photopolymerizable epoxy resin composition No. 5 was completely photo-set in 100 seconds. The pot-life thereof was 15 days.

Example 2-6

A photopolymerizable epoxy resin composition No. 6 according to the present invention was prepared by mixing the following components.

|  | Parts by Weight |
|---|---|
| Epoxy resin (Trademark "ERL 4299" made by Union Carbide Japan K.K.) | 8 |
| Tris(ethylacetoacetato)aluminum | 0.2 |
| Tris(4-fluorophenyl)(o-nitrobenzyloxy)silane | 0.55 |
| (o-nitrobenzyloxy)triphenyl silane | 0.25 |

The thus obtained photopolymerizable epoxy resin composition No. 6 was applied dropwise on a polycarbonate plate and exposed to ultraviolet light, at a position 16 cm away from the same high-pressure mercury lamp light source as that employed in Example 1-1, at a temperature of 40° C. The result was that the photopolymerizable epoxy resin composition No. 6 according to the present invention was completely photo-set in 55 seconds.

The above composition was allowed to stand at room temperature to measure the pot-life thereof, with the result that the pot-life of this composition was 9 days.

Example 2-7

A photopolymerizable epoxy resin composition No. 7 according to the present invention was prepared by mixing the following components.

|  | Parts by Weight |
|---|---|
| Epoxy resin (Trademark "ERL4299" made by Union Carbide Japan K.K.) | 8 |
| Tris(ethylacetoacetato)aluminum | 0.2 |
| Tris(4-fluorophenyl)(o-nitrobenzyloxy)silane | 0.40 |
| (o-nitrobenzyloxy)triphenyl silane | 0.40 |

The thus obtained photopolymerizable epoxy resin composition No. 7 was applied dropwise on a polycarbonate plate and exposed to ultraviolet light, at a position 16 cm away from the same high-pressure mercury lamp light source as that employed in Example 1-1, at a temperature of 40° C. The result was that the photopolymerizable epoxy resin composition No. 7 according to the present invention was completely photo-set in 53 seconds. The above composition was allowed to stand at room temperature to measure the pot-life thereof, with the result that the pot-life of this composition was 9 days.

From the results of Examples, the photopolymerizable epoxy resin compositions No. 6 and No. 7 according to the present invention are obviously improved in the photo-setting speed, without decreasing the pot-life, as compared with the photopolymerizable epoxy resin composition No. 3 according to the present invention.

When used with any of the previously mentioned aluminum compounds, the photodecomposing organosilicon compound according to the present invention serves as a catalyst for promoting the photo-setting of an epoxy resin. Such a photodecomposing organosilicon compound has an advantage over other conventional compounds that the photodecomposing organosilicon compound according to the present invention can initiate the photo-setting of the epoxy resin at lower temperatures and complete the photo-setting of the epoxy resin for a shorter time of period.

The photopolymerizable epoxy resin compositions according to the present invention are improved in not only the pot-life, but also the photo-setting time and accordingly such photopolymerizable epoxy resin compositions can be used as photo-setting adhesive agent, and photo-setting insulation material and resist material for electrical and electronical components.

What is claimed is:

1. An organosilicon compound having general formula (I)

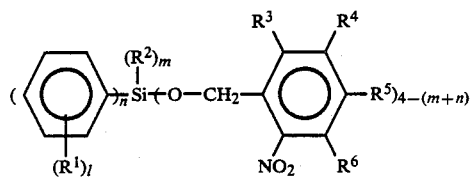

wherein $R^1$ represents fluorine; l is an integer of 1 to 5; $R^2$ represents a lower alkyl group, a lower unsaturated alkyl group or an aromatic group, $R^3$, $R^4$, $R^5$ and $R^6$ each represent hydrogen, halogen, an alkyl group, an aryl group, a nitro group, a cyano group, and an alkoxy group, which may be the same or different; m is an integer of 0 to 2, when m is 2, each $R^2$ may be the same or different; and n is an integer of 1 to 3, provided that m+n is not more than 3 (m+n≦3).

2. The organosilicon compound as claimed in claim 1, wherein said lower alkyl group or lower unsaturated alkyl group represented by $R^2$ have 1 to 6 carbon atoms, which may have as a substituent a halogen, and said aromatic group represented by $R^2$ be a phenyl group or a tolyl group, which may have a substitutent selected from the group consisting of halogen, an alkyl group, an aryl group, a nitro group, a cyano group and an alkoxyl group.

3. The organosilicon compound as claimed in claim 1, wherein said organosilicon compound is selected from the group consisting of:
(1) dimethyl(p-fluorophenyl)(o-nitrobenzyloxy)silane,
(2) bis(p-fluorophenyl)methyl(o-nitrobenzyloxy)silane,
(3) tris(p-fluorophenyl)(o-nitrobenzyloxy)silane,
(4) tris(2,4,6-trifluorophenyl)(o-nitrobenzyloxy)silane,
(5) tris(2,4,5-trifluorophenyl)(o-nitrobenzyloxy)silane,
(6) bis(p-fluorophenyl)(2-fluoroethyl)(o-nitrobenzyloxy) silane,
(7) bis(p-fluorophenyl)bis(o-nitrobenzyloxy)silane,
(8) (p-fluorophenyl)methylbis(o-nitrobenzyloxy)silane
(9) (p-flourophenyl)tri(o-nitrobenzyloxy)silane,
(10) tris(p-fluorophenyl)(2,6-dinitrobenzyloxy)silane,
(11) (2,4,6-trifluorophenyl)dimethyl(4,5-dimethoxy-2-nitrobenzyloxy)silane,
(12) bis(p-fluorophenyl)methyl(4,5,6-trimethoxy-2-nitrobenzyloxy)silane,
(13) bis(p-fluorophenyl)methyl(3,4,5-trimethoxy-2-nitrobenzyloxy)silane,
(14) (2,4,5-trifluorophenyl)methylbis(p-chloro-o-nitrobenzyloxy)silane,
(15) tris(p-flourophenyl)(p-phenoxy-o-nitrobenzyloxy) silane,
(16) bis(p-fluorophenyl)vinyl(o-nitrobenzyloxy)silane,
(17) (p-fluorophenyl)methylvinyl(o-nitrobenzyloxy)silane,
(18) (p-fluorophenyl)vinylbis(o-nitrobenzyloxy)silane,
(19) (2,4,6-trifluoropheny)-t-butylbis(o-nitrobenzyloxy) silane,
(20) bis(p-fluorophenyl)bis(3-methyl-2-nitrobenzyloxy)silane,
(21) tris(p-fluorophenyl)(5-methyl-2-nitrobenzyloxy)silane,
(22) bis(2,4,5-trifluorophenyl)bis(3-methoxy-2-nitrobezyl) silane,
(23) bis(p-fluorophenyl)bis(6-chloro-2-nitrobenzyloxy)silane,
(24) bis(p-fluorophenyl)bis(2,4-dinintrobenzyloxy)silane
(25) bis(p-fluorophenyl)phenyl(3-methyl-4-methoxy-2-nitrobenzyloxy)silane,
(26) tris(p-fluorophenyl)(3,4-dimethoxy-2-nitrobenzyloxy) silane,
(27) bis(p-fluorophenyl)phenyl(o-nitrobenzyloxy)silane,
(28) (p-fluorophenyl)diphenyl(o-nitrobenzyloxy)silane,
(29) bis(2,4,6-trifluorophenyl)phenyl(o-nitrobenzyloxy) silane,
(30) (2,4,6-trifluorophenyl)diphenyl(o-nitrobenzyloxy) silane,
(31) bis(2,4,5-trifluorophenyl)phenyl(o-nitrobenzyloxy) silane,
(32) (2,4,5-trifluorophenyl)diphenyl(o-nitrobenzyloxy) silane,

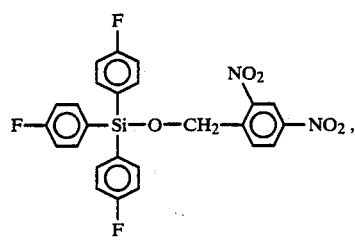

(34) 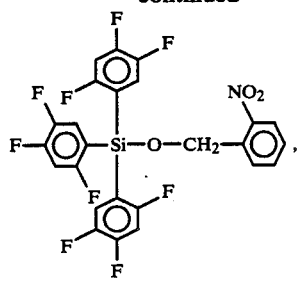

(35) 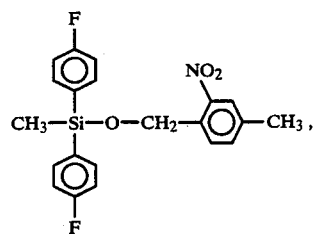

(36) 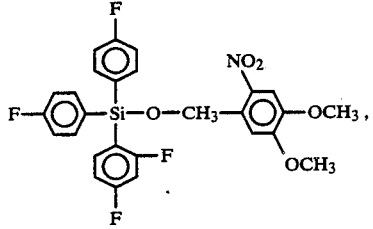

(37) 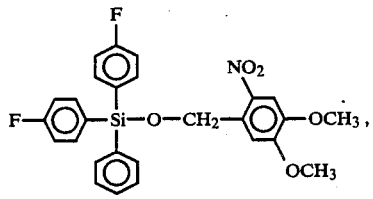

(38) 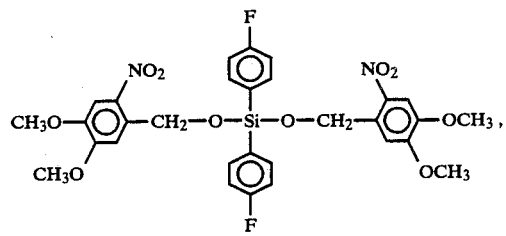

(39) 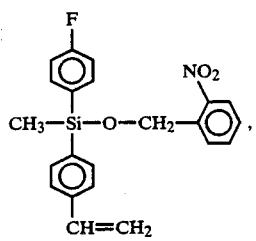

(40) 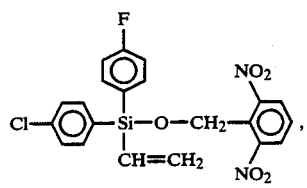

(41) 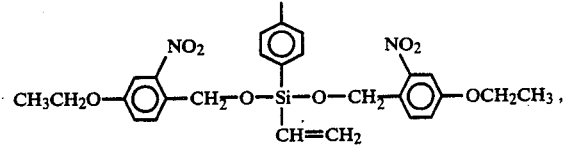

(42) 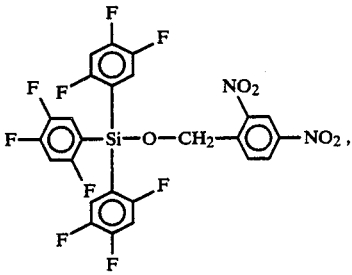

(43) 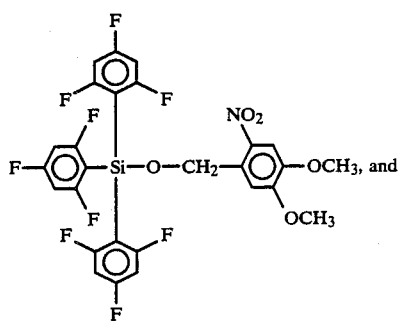

(44) 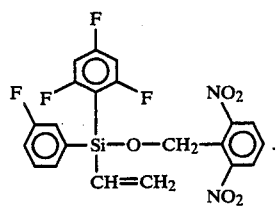

4. A photopolymerizable epoxy resin composition prepared by mixing an epoxy resin component, an photodecomposing organosilicon compound having general formula (I), and an aluminum compound:

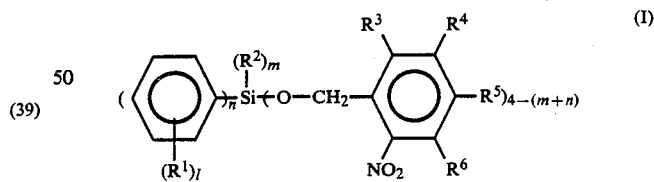

wherein $R^1$ represents fluorine; $l$ is an integer of 1 to 5; $R^2$ represents a lower alkyl group, a lower unsaturated alkyl group or an aromatic group, $R^3$, $R^4$, $R^5$ and $R^6$ each represent hydrogen, halogen, an alkyl group, an aryl group, a nitro group, a cyano group, and an alkoxyl group, which may be the same or different; m is an integer of 0 to 2, when m is 2, each $R^2$ may be the same or different; and n is an integer of 1 to 3, provided that m+n is not more than 3 ($m+n \leq 3$).

5. The photopolymerizable epoxy resin composition as claimed in claim 4, wherein said epoxy resin is such an epoxy resin as having two or more epoxy groups in each monomer unit thereof.

6. The photopolymerizable epoxy resin composition as claimed in claim 4, wherein said aluminum compound is selected from the group consisting of: tris(ethoxyacetylacetato)aluminum, tris(oxynato)aluminum, trismethoxy aluminum, trisethoxy aluminum, trisisopropoxy aluminum, trisphenoxy aluminum, isopropoxy diethoxy aluminum, trisbutoxy aluminum, trisacetoxy aluminum, trisstearato aluminum, trisbutylato aluminum, trispropionato aluminum, trisisopropionato aluminum, trisacetylacetonato aluminum, tristrifluoroacetylacetonato aluminum, trispentafluoroacetylacetonato aluminum, trisethylacetoacetato aluminum, trissalicylaldehydato aluminum, trisdiethylmalorato aluminum, trispropylacetoacetato aluminum, trisbutylacetoacetato aluminum, trisdipivaloylmethanato aluminum, diacetylacetonato dipivaloylmethanato aluminum, tris(ethylacetoacetonato)aluminum, tris(tert-butylacetoacetato)aluminum, tris(isobutylacetoacetato)aluminum, tris(ethylsalicylato)aluminum, tris(phenylsalicylato)aluminum and tris(o-acetylphenolato)aluminum.

7. The photopolymerizable epoxy resin composition as claimed in claim 4, wherein the amount of said photodecomposing organosilicon compound is in the range of 0.5 to 15 parts by weight to 100 parts by weight of said epoxy resin component.

8. The photopolymerizable epoxy resin composition as claimed in claim 4, further comprising an o-nitrobenzyl silyl ether having general formula (II):

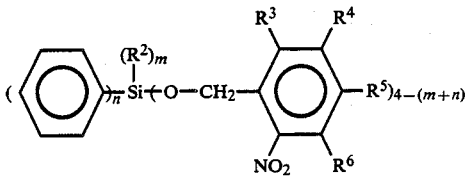

wherein $R^2$ represents a lower alkyl group, a lower unsaturated alkyl group or an aromatic group, $R^3$, $R^4$, $R^5$ and $R^6$ each represent hydrogen, halogen, an alkyl group, an aryl group, a nitro group, a cyano group, and an alkoxyl group, which may be the same or different; m is an integer of 0 to 2, when m is 2, each $R^2$ may be the same or different; and n is an integer of 1 to 3, provided that m + n is not more than 3 ($m+n \leq 3$).

9. The photopolymerizable epoxy resin composition as claimed in claim 8, wherein the amount of said o-nitrobenzyl silyl ether compound is 0.1 to 1.5 times the amount of said photodecomposing organosilicon compound of general formula (I).

* * * * *

UNITED STATES PATENT AND TRADEMARK OFFICE
CERTIFICATE OF CORRECTION

PATENT NO. : 4,954,534

DATED : September 4, 1990

INVENTOR(S) : Tetsu Yamamuro

It is certified that error appears in the above-identified patent and that said Letters Patent is hereby corrected as shown below:

Column 2, line 19, after "temperatures", insert a period (--.--).

Column 3, line 36, "R2" should read --$R^2$--.

Column 12, line 18, "m, n," should read --m and n--;
       line 19, delete "and".

Column 13, line 50, before "Epoxy resin", insert --(c)--.

Column 14 line 52, "2350" should read --350--;
       line 55, after "811", insert a comma (--,--);
       line 56, after "212", insert a comma (--,--).

Column 19, line 13, "varies" should read --vary--.

UNITED STATES PATENT AND TRADEMARK OFFICE
CERTIFICATE OF CORRECTION

PATENT NO. : 4,954,534

DATED : September 4, 1990

INVENTOR(S) : Tetsu Yamamuro

It is certified that error appears in the above-identified patent and that said Letters Patent is hereby corrected as shown below:

Column 21, line 17, "tetrahydrofulan" should read --tetrahydrofuran--.

Column 23, line 61, "photo-settting" should read --photo-setting--;

line 66, after "seconds", insert a period (--.--).

Column 25, line 22, "time of period" should read --period of time--;

line 46, "alkoxy" should read --alkoxyl--.

Column 26, lines 29-30, "(2,4,6-trifluoropheny)-t-butylbis(o-nitrobenzyloxy)silane," should read --(2,4,6-trifluorophenyl)-t-butylbis(o-nitrobenzyloxy)silane,--;

UNITED STATES PATENT AND TRADEMARK OFFICE
CERTIFICATE OF CORRECTION

PATENT NO. : 4,954,534

DATED : September 4, 1990

INVENTOR(S) : Tetsu Yamamuro

It is certified that error appears in the above-identified patent and that said Letters Patent is hereby corrected as shown below:

Column 26, lines 35-36, "bis(2,4,5-trifluorophenyl)bis(3-methoxy-2-nitrobezyl)silane," should read --bis(2,4,5-trifluorophenyl)bis(3-methoxy-2-nitrobenzyl)silane,--;

lines 39-40, "bis(p-fluorophenyl)bis(2,4-dinintrobenzyloxy)silane" should read --bis(p-fluorophenyl)bis(2,4-dinitrobenzyloxy)silane--.

Column 28, line 43, "an" (second occurrence) should read --a--.

Signed and Sealed this

Seventh Day of April, 1992

Attest:

HARRY F. MANBECK, JR.

*Attesting Officer*   *Commissioner of Patents and Trademarks*